United States Patent
Stauch et al.

(10) Patent No.: US 6,416,516 B1
(45) Date of Patent: Jul. 9, 2002

(54) ACTIVE INTRAMEDULLARY NAIL FOR THE DISTRACTION OF BONE PARTS

(75) Inventors: Roman Stauch, Assamstadt; Jurgen Klein, Igersheim, both of (DE)

(73) Assignee: Wittenstein GmbH & Co. KG, Igersheim (DE)

(*) Notice: Subject to any disclaimer, the term of this patent is extended or adjusted under 35 U.S.C. 154(b) by 0 days.

(21) Appl. No.: 09/913,431

(22) PCT Filed: Feb. 14, 2000

(86) PCT No.: PCT/EP00/01208

§ 371 (c)(1),
(2), (4) Date: Sep. 27, 2001

(87) PCT Pub. No.: WO00/48524

PCT Pub. Date: Aug. 24, 2000

(30) Foreign Application Priority Data

Feb. 16, 1999 (DE) .......................... 199 06 423

(51) Int. Cl.⁷ .............................................. A61B 17/72
(52) U.S. Cl. ...................................................... 606/62
(58) Field of Search ............................ 606/62, 63, 64, 606/67, 68, 72, 90, 105, 60

(56) References Cited

U.S. PATENT DOCUMENTS

| | | | | |
|---|---|---|---|---|
| 5,429,638 A | * | 7/1995 | Muschler et al. | 606/60 |
| 5,536,269 A | * | 7/1996 | Spievach | 606/63 |
| 5,626,579 A | * | 5/1997 | Muschler et al. | 606/60 |
| 5,626,581 A | * | 5/1997 | Staehlin et al. | 606/63 |
| 5,704,938 A | * | 1/1998 | Staehlin et al. | 606/62 |
| 5,704,939 A | * | 1/1998 | Justin | 606/63 |
| 5,961,553 A | * | 10/1999 | Coty et al. | 606/62 |
| 6,033,412 A | * | 3/2000 | Losken et al. | 606/105 |

FOREIGN PATENT DOCUMENTS

| WO | 9625117 | * | 8/1996 | .................. 606/62 |

\* cited by examiner

*Primary Examiner*—Eduardo C. Robert
(74) *Attorney, Agent, or Firm*—Bachman & LaPointe, P.C.

(57) ABSTRACT

An intromedullary nail for the distraction of bone parts consists of two elements which can be moved relative to one another. At least one electrically operated driving element which is supplied by electrical energy to move the two elements relative to one another is connected to the medullary nail by at least one detachable plug-in element.

10 Claims, 3 Drawing Sheets

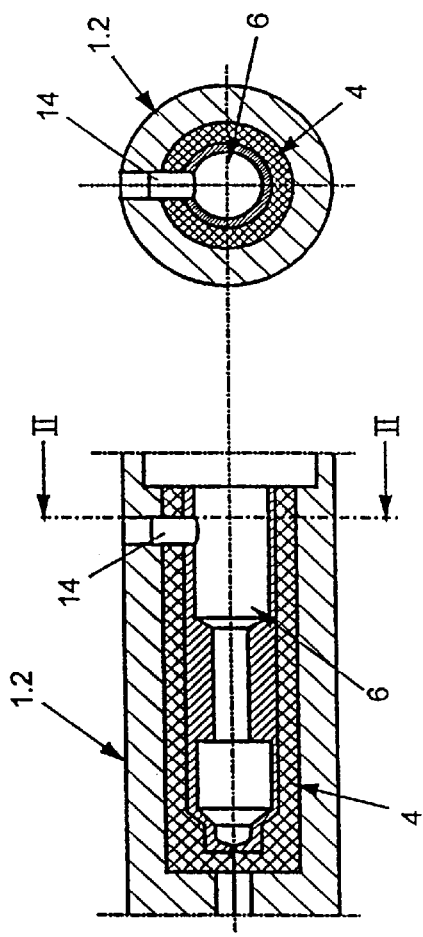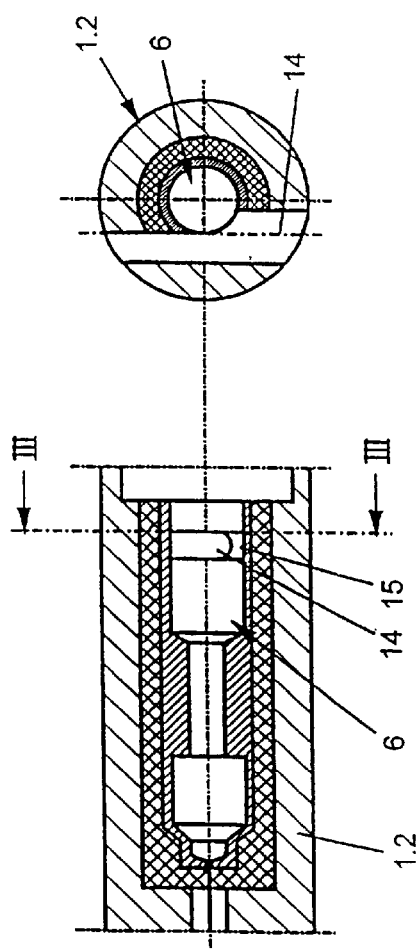

ACTIVE INTRAMEDULLARY NAIL FOR THE DISTRACTION OF BONE PARTS

BACKGROUND OF THE INVENTION

The present invention relates to an active medullary nail for distraction of bone segments, comprising two elements, prosthesis, or the like, which can be moved relative to each other, with at least one electrically operated drive element.

Medullary nails of this type are known and available on the market in a very wide variety of forms and designs. It is becoming more and more common for electrical drive elements to be provided in the medullary nails in order to generate a distraction of two elements which are movable relative to each other. To do this, electrical connections are necessary for operating the medullary nail.

A disadvantage of the previously known connections is that these are embedded directly in the medullary nail and are often broken or damaged as a result of being moved many times if distraction takes place over a certain period of time, or as a result of external influences, for example movement of the limbs.

A further disadvantage is that these connections are removed following a specified distraction, for example by surgery or being cut through. Then, in the event of a renewed distraction, this connection has to be surgically connected up again, which is time-consuming.

It is an object of the present invention to make available an active medullary nail for distraction and also a medullary nail with optionally attached prostheses or the like, with which an electrical connection can be established in a very simple way. This is intended to fulfill the electrical, mechanical and hygiene requirements.

SUMMARY OF THE INVENTION

To achieve this object, the electrical energy can be delivered to the medullary nail via at least one detachable plug element.

A socket is provided in an opening preferably at one end of one of the two axially displaceable elements of the medullary nail. A plug element can be inserted there into an opening in order to establish an electrical connection for control and energy transmission. In this arrangement, completely standard plugs or plug connections can be used, as are described for example in DIN-ISO 5841-3. A bipolar design is preferred. A plurality of electrical signals can be transmitted.

It has proven particularly advantageous for at least one sealing lip element to be assigned to the plug element, preferably at the end. This sealing lip element is elastic and is preferably designed tapering outward. It closes off the opening of the socket completely and in an absolutely leaktight manner. In this way, no tissue fluid or the like can gain entry and damage the electrical connection between socket and plug element.

It is also advantageous in the present invention that the medullary nail be designed as a prosthesis and that after a desired period of distraction only the electrical plug connection be surgically removed. The opening can then be closed with a stopper or the like. Should further distraction prove necessary, the stopper can be surgically removed again and the plug then inserted there. This affords considerable advantages in particular in operating and handling active medullary nails of this type.

BRIEF DESCRIPTION OF THE DRAWINGS

Further advantages, features and details of the invention will become apparent from the following description of preferred illustrative embodiments and from the drawing, in which:

FIG. 2a shows an at least partial longitudinal section through the medullary nail according to FIG. 1;

FIG. 2b shows a cross section through the medullary nail along the line II—II according to FIG. 2a;

FIG. 3a shows a partial longitudinal section through the medullary nail according to FIG. 1 as a further illustrative embodiment;

FIG. 3b shows a cross section through the medullary nail according to FIG. 3a along the line III—III;

DETAILED DESCRIPTION

Figure 1:
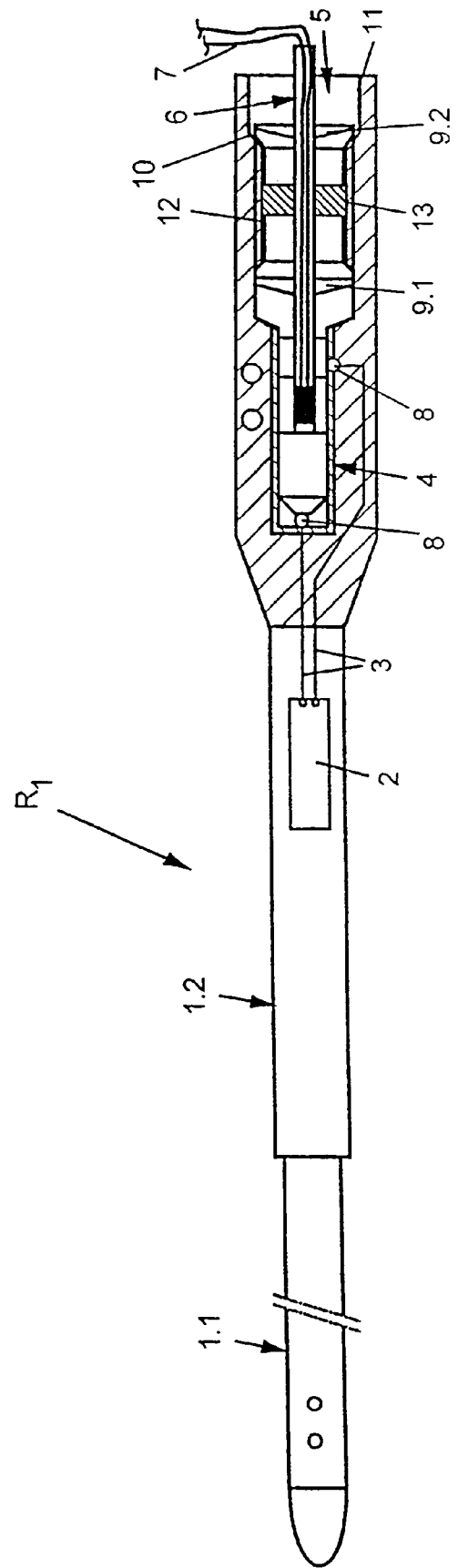
FIG. 1 shows a diagrammatic view of an at least partially opened active medullary nail.

According to FIG. 1, an active medullary nail $R_1$ according to the invention has two elements 1.1, 1.2 which can be moved axially relative to each other. In the preferred illustrative embodiment, the element 1.1 can be displaced relative to the element 1.2. Drive means (not shown here) such as gears, push rods, shape-memory drives or the like can move the element 1.1 relative to the element 1.2. At least one electrical drive element 2 is preferably provided in the element 1.2 of the medullary nail $R_1$. This drive element 2 communicates with a socket 4 of the element 1.2 via electrical connection lines 3. The socket 4 is provided at the end face of the element 1.2 in the medullary nail. A plug element 6 can be inserted into the socket 4 through an opening 5. Connected to the plug element 6 there are energy supply lines 7 which lead for example to an external power source. From there, energy can be introduced directly or indirectly, for example by induction. This energy is required for operating and controlling the drive element 2.

To ensure that a desired distraction can take place over a certain period of time while the active medullary nail $R_1$ is in the bone, it is necessary to permanently establish an electrical connection. In this respect it has proven particularly advantageous to insert what is known as a plug element 6 into the end, particularly the end face, of the element 1.2. Corresponding contact points 8 transmit electrical energy and/or electrical signals.

However, an important aspect of such connections is that for hygiene reasons there must be an absolutely leaktight and clean detachable connection point between medullary nail $R_1$ and plug element 6. For this purpose, at least one sealing lip element 9.1, 9.2 is assigned to the plug element 6 and closes off in a detachable manner the opening 5 and thus the socket 4 of the element 1.2. By this means it is possible to ensure that an electrical contact remains established in a detachable manner over long periods of time.

The outer sealing lip element 9.2 also ensures an optimum protection against buckling, which is of importance given the bending stresses which occur.

Figure 4:
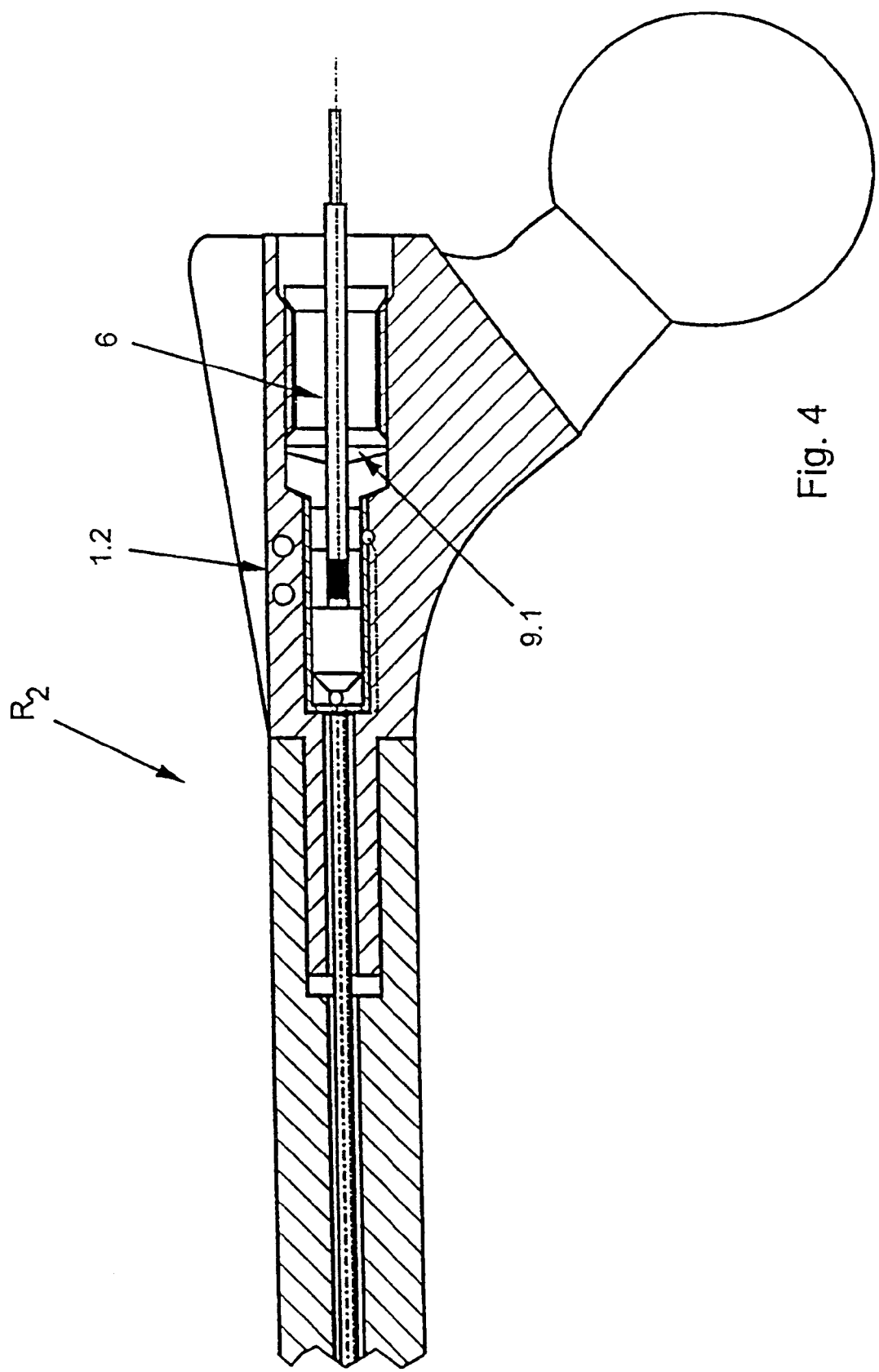
FIG. 4 shows an at least partial longitudinal section through a further illustrative embodiment of a medullary nail according to FIG. 1.

If, for example, the active medullary nail is a hip-joint endoprosthesis, as is shown partially in FIG. 4, or a knee-joint endoprosthesis, this too can be provided with a corresponding plug connection, as described above. In this way, a correction can be made for example after the operation by means of a corresponding distraction. This correction can be carried out over a fairly long period of the recovery process. If no further correction is then necessary, for example, only the plug element is removed from the opening 5 of the element 1.2. If appropriate, the opening 5 is closed with a tight stopper or the like should correction be necessary again. In this way, prostheses designed as active medullary nails $R_1$ can be operated permanently and, after an appropriate distraction or correction of the bone, the electrical connections can be removed without difficulty.

Should a further correction prove necessary after a certain length of time, the plug element can be introduced again into the opening. An optionally fully implantable subcutaneous energy source, to which energy or corresponding signals are inductively fed, can then be implanted under the skin. The active medullary nail can be put back into operation in this way.

Also of importance is a radial sealing lip element 9.1, 9.2 which if appropriate bears on an inwardly projecting shoulder 10. The sealing lip element 9.1, 9.2 is preferably designed tapering outward and lies tightly on an inner wall 11 of the socket 4 or element 1.2.

It is also intended to provide an internal thread 12 inside the socket 4, in which a corresponding external thread 13 of the plug element 6 engages in order to secure the plug element 6 in a detachable manner. However, locking connections or the like are preferably used.

As a means of securing against removal during operation, simple threaded pins or the like can be provided, as are indicated for example in FIG. 2a. There, a corresponding securing element 14 passes radially through the element 1.2 as a threaded pin in order to detachably secure and clamp the plug element 6 which has been inserted in the socket 4. This is also illustrated in the cross-sectional representation in FIG. 2b.

FIGS. 3a and 3b show a further securing element 14 which engages in a corresponding groove 15 of the plug element 6 and thus axially secures the plug element 6 relative to the socket 4 of the element 1.2. The securing element 14 can in this case be provided as a bolt or the like in order to prevent an axial movement of the plug element 6 relative to the socket 4. No restriction is placed on the invention in this regard.

In the last illustrative embodiment according to FIG. 4, it will be seen that plug elements 6 can also be inserted, in the manner described above, as active medullary nails $R_2$ in any desired prostheses, hip joint endoprostheses. This is intended also to lie within the scope of the present invention.

LIST OF REFERENCE LABELS

| List of reference labels | |
| --- | --- |
| 1 | Element |
| 2 | Drive element |
| 3 | Connection line |
| 4 | Socket |
| 5 | Opening |
| 6 | Plug element |
| 7 | Connection line |
| 8 | Contact point |
| 9 | Sealing lip element |
| 10 | Shoulder |
| 11 | Inner wall |
| 12 | Internal thread |
| 13 | External thread |
| 14 | Securing element |
| 15 | Groove |
| $R_1$ | Active medullary nail |
| $R_2$ | Active medullary nail |

What is claimed is:

1. An active medullary nail comprising:

a first element and a second element;

electrically operated drive means connected to one of said first element and said second element for moving same relative to each other; and a detachable plug element mounted into an opening on said one of said first element and said second element, wherein electrical energy is delivered via said detachable plug element to the electrically operated drive means for moving said first element and said second element relative to each other.

2. The active medullary nail as claimed in claim 1, wherein said plug element engages detachably in a socket on said one of said first element and said second element to establish at least one electrical contact point.

3. The active medullary nail as claimed in claim 2, wherein at least one sealing lip element is mounted on said plug element.

4. The active medullary nail as claimed in claim 3, wherein said at least one sealing lip element is arranged radially on said plug element.

5. The active medullary nail as claimed in claim 3, wherein said at least one sealing lip element tapers outward from said plug element.

6. The active medullary nail as claimed in claim 3, wherein said sealing lip element closes off said opening and bears an inner shoulder defining at least in part said opening.

7. The active medullary nail as claimed in claim 1, wherein said plug element is secured against removal in said opening by means of a securing element.

8. The active medullary nail as claimed in claim 7, wherein said securing element at least partially engages axially in said plug element and holds said plug element in a detachable manner relative to said one of said first element and said second element.

9. The active medullary nail as claimed in claim 1, wherein said opening is provided with an internal thread into which a matching external thread of said plug element engages for securing and fixing said plug element.

10. The active medullary nail as claimed in claim 1, wherein an energy source comprising a fully implantable inductive energy source for inductive energy transfer is connected to said plug element.

* * * * *